US00PP36626P3

(12) United States Plant Patent
Moerman

(10) Patent No.: US PP36,626 P3
(45) Date of Patent: Apr. 22, 2025

(54) ***LAVANDULA* PLANT NAMED 'AGRI812'**

(50) Latin Name: *Lavandula stoechas*
Varietal Denomination: AGRI812

(71) Applicant: Marcel Moerman, De Lier (NL)

(72) Inventor: Marcel Moerman, De Lier (NL)

(73) Assignee: AGRIVERCO GENETICS B.V., De Lier (NL)

( * ) Notice: Subject to any disclaimer, the term of this patent is extended or adjusted under 35 U.S.C. 154(b) by 130 days.

(21) Appl. No.: 18/227,123

(22) Filed: Jul. 27, 2023

(65) Prior Publication Data

US 2025/0040459 P1 Jan. 30, 2025

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Lavandula* plant named 'AGRI812', characterized by its upright to outwardly and broadly spreading plant habit; freely branching growth habit; freely flowering habit; relatively large dark violet-colored flowers and purple-colored terminal flower bracts positioned on strong and erect peduncles; long flowering period; and good garden performance.

2 Drawing Sheets

Figure 1:
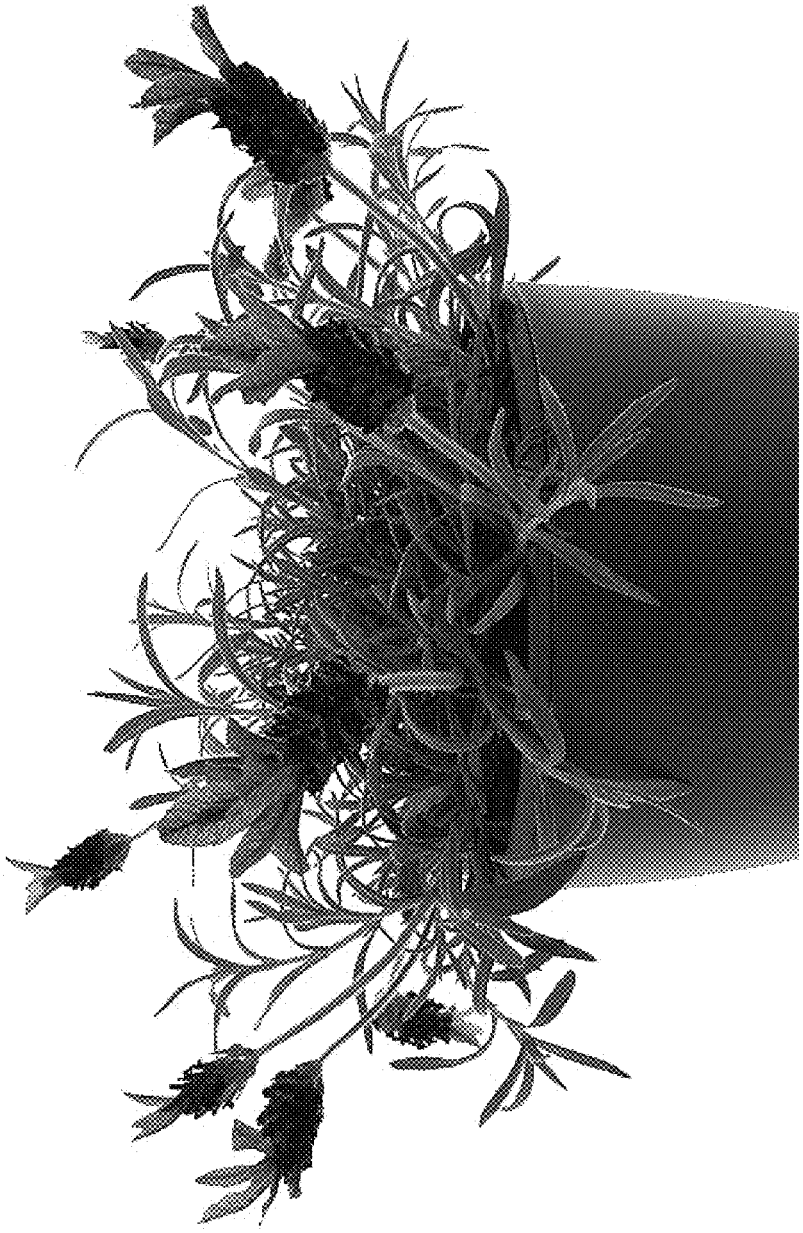

Botanical designation: *Lavandula stoechas.*
Cultivar denomination: 'AGRI812'.

CROSS-REFERENCED TO CLOSELY-RELATED APPLICATIONS

An United Kingdom Plant Breeder's Rights application for the instant plant was filed by the Inventor and the Assignee, Agriverco Genetics B.V. on Jun. 27, 2023, application number to be determined. Foreign priority is not claimed to this application.

An European Community Plant Breeder's Rights application for the instant plant was filed by the Inventor and his European company, Labreco Europe B.V. on Jul. 11, 2023, application number 2023/1504. Foreign priority is not claimed to this application.

BACKGROUND OF THE INVENTION

The present invention relates to a new and distinct *Lavandula* plant, botanically known as *Lavandula stoechas*, commonly referred to as Lavender and hereinafter referred to by the name 'AGRI812'.

The new *Lavandula* plant is a product of a planned breeding program conducted by the Inventor in De Lier, The Netherlands. The objective of the breeding program was to develop new unique *Lavandula* plants with long flowering period and attractive plant form and flower coloration.

The new *Lavandula* plant originated from a cross-pollination in July 2015 of a proprietary selection of *Lavandula stoechas* identified as code designation agri 279, not patented, as the female, or seed, parent with a proprietary selection of *Lavandula stoechas* identified as code designation agri 425, not patented, as the male, or pollen, parent. The new *Lavandula* plant was discovered and selected by the Inventor as a single flowering plant within the progeny of the stated cross-pollination in a controlled environment in De Lier, The Netherlands in April 2016.

Asexual reproduction of the new *Lavandula* plant by terminal cuttings in a controlled greenhouse environment in De Lier, The Netherlands since May 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'AGRI812' as a new and distinct *Lavandula* plant:

1. Upright to outwardly and broadly spreading plant habit.
2. Freely branching growth habit.
3. Freely flowering habit.
4. Relatively large dark violet-colored flowers and purple-colored terminal flower bracts positioned on strong and erect peduncles.
5. Long flowering period.
6. Good garden performance.

Plants of the new *Lavandula* differ primarily from plants of the female parent selection primarily in leaf size and color as plants of the new *Lavandula* have broader and more greyed-colored leaves than plants of the female parent selection.

Plants of the new *Lavandula* differ primarily from plants of the male parent selection primarily in growth habit as plants of the new *Lavandula* are more outwardly spreading than and not as upright as plants of the male parent selection. In addition, plants of the new *Lavandula* have larger terminal flower bracts than plants of the male parent selection.

Plants of the new *Lavandula* can be compared to plants of the *Lavandula stoechas* 'Dark Knight', not patented. In side-by-side comparisons, plants of the new *Lavandula* differ primarily from plants of 'Dark Knight' in the following characteristics:

1. Plants of the new *Lavandula* are more outwardly spreading than and not as upright as plants of 'Dark Knight'.
2. Plants of the new *Lavandula* have larger flowers than plants of 'Dark Knight'.
3. Plants of the new *Lavandula* have larger terminal flower bracts than plants of 'Dark Knight'.

Plants of the new *Lavandula* can also be compared to plants of the *Lavandula stoechas* 'AGRI811', disclosed in U.S. Plant Pat. No. 33,173. In side-by-side comparisons, plants of the new *Lavandula* differ primarily from plants of 'AGRI811' in the following characteristics:

1. Plants of the new *Lavandula* are more freely branching than plants of 'AGRI811'.
2. Plants of the new *Lavandula* have darker green-colored leaves than plants of 'AGRI811'.
3. Plants of the new *Lavandula* are not as freely flowering as plants of 'AGRI811'.
4. Plants of the new *Lavandula* have more terminal flower bracts per flower than plants of 'AGRI811'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'AGRI812' grown in a container.

Figure 2:
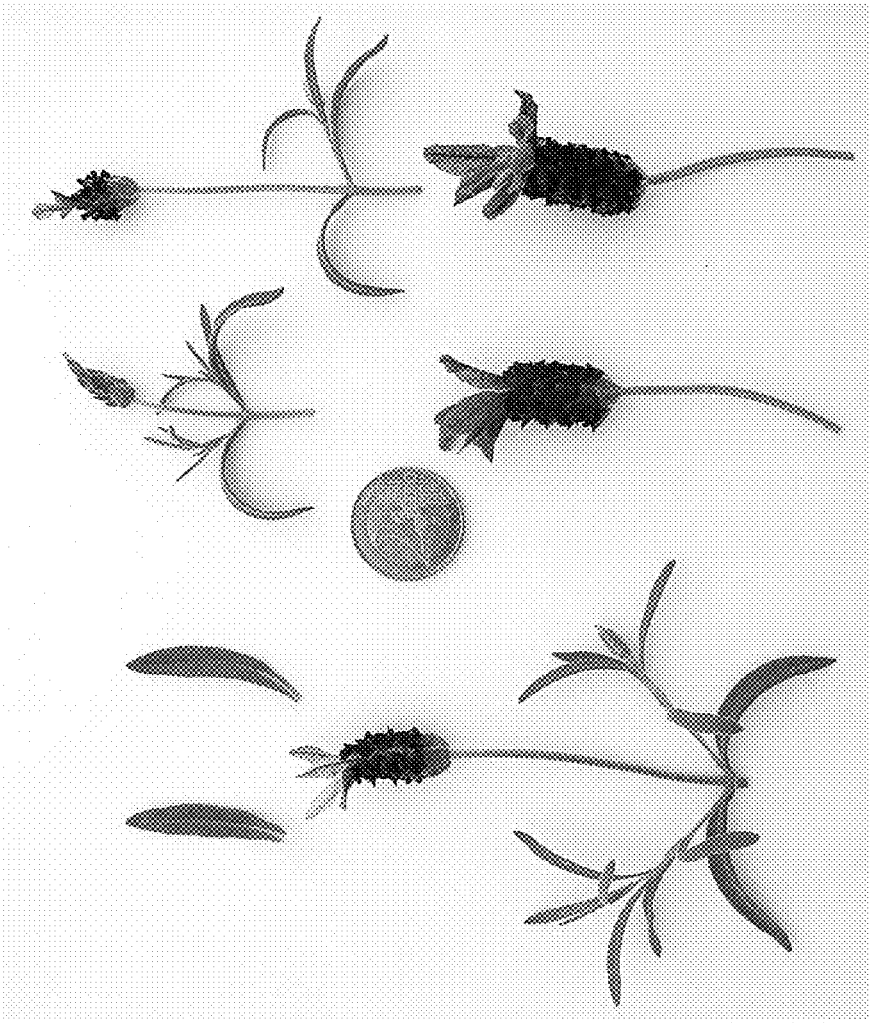

The photograph on the second sheet (FIG. 2) are close-up views of typical leaves, developing inflorescences and fully developed inflorescences.

DETAILED BOTANICAL DESCRIPTION

Plants used in the aforementioned photographs and following detailed description were grown in 12-cm containers during the spring in an outdoor nursery in Maasdijk, The Netherlands and under cultural practices typical of commercial *Lavandula* production. Plants were pinched four weeks after planting and were six months old when the photographs and description were taken. During the production of the plants, day temperatures ranged from 18 C to 20 C and night temperatures ranged from 8 C to 10 C. In the following description, color references are made to The Royal Horticultural Society Colour Chart, 2015 Edition, except where general terms of ordinary dictionary significance are used.

Botanical classification: *Lavandula stoechas* 'AGRI812'.

Parentage:

*Female, or seed, parent*.—Proprietary selection of *Lavandula stoechas* identified as code designation agri 279, not patented.

*Male, or pollen, parent*.—Proprietary selection of *Lavandula stoechas* identified as code designation agri 425, not patented.

Propagation:

*Type*.—Terminal vegetative cuttings.

*Time to initiate roots, summer*.—About two weeks at temperatures about 18 C.

*Time to initiate roots, winter*.—About three weeks at temperatures about 18 C.

*Time to produce a rooted young plant, summer*.—About three weeks at temperatures about 18 C.

*Time to produce a rooted young plant, winter*.—About four weeks at temperatures about 18 C.

*Root description*.—Medium in thickness, fleshy; typically creamy white in color, actual color of the roots is dependent on substrate composition, water quality, fertilizer type and formulation.

*Rooting habit*.—Low branching; sparse.

Plant description:

*Plant and growth habit*.—Herbaceous perennial; upright to outwardly and broadly spreading plant habit; flattened globular in overall plant shape; freely branching habit; moderately vigorous growth habit and moderate growth rate; flowers arranged in verticillasters on crowded spikes with showy terminal flower bracts.

*Plant height, soil level to top of foliar plane*.—About 11.8 cm.

*Plant height, soil level to top of floral plane*.—About 12.5 cm.

*Plant width*.—About 25.3 cm.

*Lateral branch description*.—Quantity per plant: Freely branching habit with about 15 primary lateral branches each with about ten secondary lateral branches developing per plant. Length: About 8.1 cm. Diameter: About 2 mm. Internode length: About 1.7 cm. Strength: Moderately strong. Aspect: Primary lateral branches, upright to about 90 degrees from vertical; secondary lateral branches, about 30 to 50 degrees from primary lateral branch axis. Texture and luster: Moderately to densely tomentose; matte. Color, when developing: Close to 146D. Color, developed: Close to 138B with venation, close to 138A; with development, close to N199A, N199C and 200B.

*Leaf description*.—Arrangement: Opposite, simple; sessile. Length: About 4.3 cm. Width: About 8 mm. Shape: Narrowly oblong to narrowly elliptic. Apex: Acute. Base: Cuneate. Margin: Entire; slightly revolute; not lobed. Texture and luster, upper and lower surfaces: Densely glandular pubescent; not rugose; matte. Fragrance: Strongly aromatic, pungent. Venation pattern: Pinnate. Color: Developing leaves, upper surface: Close to 138A. Developing leaves, lower surface: Close to 143A. Fully expanded leaves, upper surface: Close to NN137A; venation, close to 146D. Fully expanded leaves, lower surface: Close to NN137D; venation, slightly lighter than NN137D.

Flower description:

*Flower type, arrangement and habit*.—Single salverform flowers arranged in compact verticillasters on crowded terminal spikes; freely flowering, about 100 flowers developing per inflorescence and about 1,300 flowers developing per plant; flowers with two-lobed upper lip and three-lobed lower lip; flowers face mostly outwardly on the spike; inflorescences with showy terminal flower bracts; flowers sessile.

*Natural flowering season*.—Long flowering period; continuous from late spring into the summer in The Netherlands.

*Flower longevity on the plant*.—Inflorescences last about four weeks on the plant; flowers not persistent.

*Fragrance*.—None detected.

*Flower buds*.—Length: About 6 mm. Diameter: About 1.5 mm. Shape: Oblong. Texture and luster: Densely tomentose; matte. Color: Close to 145B; distally, close to 146B and at the apex, close to a blend of N87A, N88A and N92A.

*Inflorescence size*.—Height, excluding terminal flower bracts: About 3 cm. Height, including terminal flower bracts: About 5 cm. Diameter, at terminal flower bracts: About 2.9 cm. Diameter, below flower bracts: About 1.5 cm.

*Flower size*.—Diameter: About 4 mm by 4.5 mm. Depth (height): About 8 mm. Throat diameter: About 1.25 mm. Tube length: About 5 mm. Tube diameter: About 1 mm.

*Petals*.—Quantity and arrangement: Upper lip, two-lobed and lower lip, three-lobed. Length, upper lip: About 3 mm. Length, lower lip: About 2 mm. Width, upper lip: About 1.5 mm. Width, lower lip: About 1.25 mm. Shape: Roughly spatulate; lower 62.5% fused into a tube. Apex: Obtuse, rounded. Margin: Entire; slightly undulate. Texture and luster, upper surface: Smooth, glabrous; velvety; matte. Texture and luster, lower surface: Smooth, glabrous; slightly velvety; matte. Texture, throat: Smooth, glabrous; moderately velvety; matte. Texture, tube: Smooth, glabrous; matte. Color: When opening, upper surface: Upper petals, close to N92A; lower petals, close to a blend of N92A and N92B. When opening, lower surface: Close to 86A. Fully opened, upper surface: Close to a blend of N92A and N92B; venation, close to a blend of N92A and N92B; color does not change with subsequent development. Fully opened, lower surface: Close to 86A; venation, close to 86A; color does not change with subsequent development. Throat: Close to 86A; venation, close to 86A. Tube: Close to 86A fading proximally to close to N155A; venation, close to 86A fading proximally to close to N155A.

*Terminal flower bracts*.—Quantity and arrangement: About six to nine positioned at the inflorescence apex. Length: About 7 mm to 27 mm. Width: About 1 mm to 11 mm. Shape: Narrowly elliptic to oblanceolate. Apex: Bluntly acute. Base: Acuminate. Margin: Entire; moderately undulate. Texture and luster, upper and lower surfaces: Moderately to densely pubescent; matte. Color, upper surface: Close to between 77A and 77B; midvein, close to N77A. Color, lower surface: Close to between 77A and 77B; midvein, close to N79B.

*Basal flower bracts*.—Quantity and arrangement: Each group of five flowers is subtended by a single basal flower bract. Length: About 7 mm. Width: About 7 mm. Shape: Rhomboidal. Apex: Abruptly acute. Base: Broadly acuminate. Margin: Proximally, entire; distally, finely dentate. Texture and luster, upper surface: Mostly glabrous with pubescence along margins; slightly glossy. Texture and luster, lower surface: Densely tomentose; matte. Color, upper surface: Close to 71B to 71C, fading towards the base to close to 157D; venation, close to 146A. Color, lower surface: Close to 71B, fading towards the base to close to 157B; venation, close to 146A and 146B.

*Sepals*.—Quantity and arrangement: Five, lower 85% of the sepals are fused into a campanulate tube. Calyx length: About 5 mm. Calyx diameter: About 1.5 mm. Length: About 5 mm. Width: About 0.75 mm. Shape: Linear. Apex: Acute to obtuse. Margin: Entire. Texture and luster, upper surface: Smooth, glabrous; glossy. Texture and luster, lower surface: Densely pubescent; slightly glossy. Color: When opening and fully opened, upper surface: Close to 145D; venation, close to 144B. When opening and fully opened, lower surface: Close to 145B; venation, close to 146B.

*Peduncles*.—Length: About 5.5 cm. Diameter: About 2 mm. Aspect: Mostly upright. Strength: Strong. Texture and luster: Densely tomentose; matte. Color: Close to 138A.

*Reproductive organs*.—Stamens: Quantity per flower: Four. Filament length: About 1 mm. Filament color: Close to 86D. Anther shape: Short oblong; dorsifixed. Anther size: About 0.75 mm by 0.75 mm. Anther color: Close to 163C. Pollen amount: Scarce. Pollen color: Close to 15B. Pistils: Quantity per flower: One. Pistil length: About 3.5 mm. Stigma shape: Club-shaped. Stigma diameter: About 0.5 mm. Stigma color: Close to N186B. Style length: About 3 mm. Style color: Close to N155A. Ovary color: Close to 144B.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40 C and to be suitable for USDA Hardiness Zones 7 to 10.

It is claimed:

1. A new and distinct *Lavandula* plant named 'AGRI812' as herein illustrated and described.

* * * * *